US008852259B2

(12) United States Patent
Oka et al.

(10) Patent No.: US 8,852,259 B2
(45) Date of Patent: Oct. 7, 2014

(54) INDWELLING DEVICE FOR TUBULAR MEDICAL TREATMENT INSTRUMENT AND FRONT TIP OF INDWELLING DEVICE FOR TUBULAR MEDICAL TREATMENT INSTRUMENT

(75) Inventors: Katsuhiko Oka, Kyoto (JP); Yoshihiko Yokoi, Tokyo (JP); Kazumi Akita, Bungo-Ono (JP)

(73) Assignees: Katsuhiko OKA, Kyoto-shi (JP); Yoshihiko Yokoi, Tokyo (JP); Kawasumi Laboratories, Inc., Saiki-shi (JP)

( * ) Notice: Subject to any disclaimer, the term of this patent is extended or adjusted under 35 U.S.C. 154(b) by 12 days.

(21) Appl. No.: 13/322,690

(22) PCT Filed: May 25, 2010

(86) PCT No.: PCT/JP2010/058818
§ 371 (c)(1),
(2), (4) Date: Jan. 18, 2012

(87) PCT Pub. No.: WO2010/137583
PCT Pub. Date: Dec. 2, 2010

(65) Prior Publication Data
US 2012/0116413 A1    May 10, 2012

(30) Foreign Application Priority Data
May 27, 2009    (JP) .................. 2009-128157

(51) Int. Cl.
*A61F 2/06* (2013.01)
*A61F 2/966* (2013.01)
*A61F 2/07* (2013.01)

(52) U.S. Cl.
CPC ......... *A61F 2/966* (2013.01); *A61F 2002/9665* (2013.01); *A61F 2250/006* (2013.01); *A61F 2/07* (2013.01)
USPC ......................................... 623/1.11

(58) Field of Classification Search
USPC ......... 606/108, 191, 194, 198, 200; 623/1.11, 623/1.12, 1.23, 2.11
See application file for complete search history.

(56) References Cited

U.S. PATENT DOCUMENTS

2005/0090834 A1 *  4/2005  Chiang et al. .................. 606/108
2008/0039925 A1 *  2/2008  Ishimaru et al. .............. 623/1.12

FOREIGN PATENT DOCUMENTS

EP        1 982 677       10/2008
JP     2000 262632         9/2000

(Continued)

OTHER PUBLICATIONS

English machine translation from JPO for JP 2000-350785 A.*

(Continued)

*Primary Examiner* — Katherine M Shi
(74) *Attorney, Agent, or Firm* — Oblon, Spivak, McClelland, Maier & Neustadt, L.L.P.

(57) ABSTRACT

A tubular medical treatment instrument indwelling device for indwelling a stent graft expandable in the radial direction, includes a tubular sheath, a rod member configured to move forward and backward inside the sheath along the axial direction of the sheath, and a front tip provided in the forward end portion of the rod member and includes, formed therein, an engaging portion being engageable with an engagement portion provided in the stent graft. The engaging portion is formed in a position where it is hided inside the sheath when the forward end portion of the sheath is sealed with the front tip. The tubular medical treatment instrument indwelling device is capable of inhibiting damaging of a blood vessel or freeing of parietal thrombus/parietal atheroma from occurring.

3 Claims, 5 Drawing Sheets

(56) References Cited

FOREIGN PATENT DOCUMENTS

| JP | 2000-350785 A | * | 12/2000 |
| WO | WO 97/48343 | | 12/1997 |
| WO | WO 00/71059 | | 11/2000 |
| WO | 2009 028272 | | 3/2009 |

OTHER PUBLICATIONS

International Search Report Issued Jun. 22, 2010 in PCT/JP10/058818 Filed May 25, 2010.

Extended European Search Report dated Apr. 23, 2014 in European Application No. 10780538.4.

* cited by examiner

INDWELLING DEVICE FOR TUBULAR MEDICAL TREATMENT INSTRUMENT AND FRONT TIP OF INDWELLING DEVICE FOR TUBULAR MEDICAL TREATMENT INSTRUMENT

TECHNICAL FIELD

This invention relates to a tubular medical treatment instrument indwelling device for safely and reliably placing a tubular medical treatment instrument such as a stent or a stent graft for treating aneurysm, etc., at a diseased site in the medical treatment of an artery-expanding disease (aneurysm), an artery-constricting disease or other disease that occurs in a blood vessel or lumen and a front tip of a indwelling device for a tubular medical treatment instrument.

BACKGROUND ART

A stent refers to a tubular instrument that expands a stenosed site, etc., in order to secure a necessary lumen region when a blood vessel or a lumen inside a living organism is stenosed or occluded, which has a structure constituted by folding a small-gage wire of a metal, etc., in a zigzag form or rendering it network-structured and forming it into the form of a cylinder (tube).

A stent graft is an instrument obtained by applying a cylindrical structured body, composed, for example, of a polyester, etc., to an inside or outside of a cylindrical stent and suturing them together. This stent graft is inserted into a living body in a compressed state with a reduced diameter, and is delivered to a diseased site where aneurysm is developed, and is expanded at the diseased site in the radial direction and indwelled there, thus this stent graft constitutes a kind of artificial blood vessel and consequently can close said aneurysm and secure the bloodstream path.

As a indwelling device for placing a stent graft in a diseased site, conventionally, a stent graft indwelling device is known in which a front tip is provided in the forward end portion of a rod member (called pushing rod or dilator as well) (for example, see Patent Documents 1 to 3). In the front tip, there is formed a groove for hook engagement (hook engagement groove) that is engageable with a hook attached to the forward end portion of the stent graft.

According to the conventional stent graft indwelling device, the groove for the above hook engagement is formed in the front tip, so that the position of the indwelling site of the stent graft is determined while the hook and the groove are engaged with each other, and then the front tip is moved such that the engagement state is released, whereby the stent graft can be relatively easily placed in the intended position.

PRIOR ART DOCUMENTS

Patent Documents

[Patent Document 1] International Publication No. 2005/99806
[Patent Document 2] JP2000-262632A
[Patent Document 3] JP2000-350785A

SUMMARY OF THE INVENTION

Problems to be Solved by the Invention

Meanwhile, the present inventors have found that the conventional stent graft indwelling device has the following problem. That is, in the conventional stent graft indwelling device, a tubular sheath forward end portion for encasing the stent graft therein is sealed with a front tip, and in this case, the above hook engagement groove comes into a state where it is exposed outside, so that the hook engagement groove sometimes gets stuck with a blood vessel wall, etc., and inflicts a damage to the blood vessel, etc., or sometimes dislodges a parietal thrombus/parietal atheroma free.

The above problem is not limited to the stent graft indwelling device. For example, it can also take place in a tubular medical treatment instrument indwelling device for placing a tubular medical treatment instrument other than the stent graft at a diseased site, such as a stent indwelling device for placing a stent which is expandable in the radial direction.

Therefore, this invention has been made to overcome the above problems that the present inventors have found, and it is an object of this invention to provide a tubular medical treatment instrument indwelling device for placing a tubular medical treatment instrument such as a stent or a stent graft at a diseased site, which is capable of inflicting no damage to a blood vessel, etc., and constraining the occurrence of dislodging a parietal thrombus/parietal atheroma, and front tip for a tubular medical treatment instrument indwelling device.

Means to Solve the Problems

According to this invention, the following tubular medical treatment instrument indwelling devices are provided.

[1] The tubular medical treatment instrument indwelling device 1 of this invention is a tubular medical treatment instrument indwelling device 1 for delivering a radially expandable tubular medical treatment instrument SG up to a diseased site and placing the same at the diseased site, which comprises a tubular sheath 10 having flexibility and being so constituted as to encase said tubular medical treatment instrument SG therein, a rod member 30 that is so constituted as to move forward and backward inside said sheath 10 along the axial direction of said sheath, and a front tip 40 that is provided in the forward end portion of said rod member 30 and has, formed therein, an engaging portion 42 being engageable with an engagement portion H provided in said tubular medical treatment instrument SG, said front tip 40 being capable of sealing the forward end portion of said sheath 10 in a state in which it is engaged with said tubular medical treatment instrument SG, and said engaging portion 42 being formed in a position where it is hidden inside said sheath 10 when the forward end portion of said sheath 10 is sealed with said front tip 40.

According to the tubular medical treatment instrument indwelling device of this invention, therefore, the engaging portion 42 of the front tip 40 is formed in a position where it is hidden inside the sheath when the forward end portion of the sheath 10 is sealed with the front tip, so that the engaging portion 42 is no longer exposed outside when it is moved inside a blood vessel, etc. As a result, the engaging portion 42 can be constrained from inflicting a damage to a blood vessel, etc., by getting stuck on a blood vessel wall, or from dislodging a parietal thrombus/parietal atheroma free from the blood vessel wall.

According to the tubular medical treatment instrument indwelling device of this invention, there can be provided a tubular medical treatment instrument indwelling device constrained from inflicting a damage to a blood vessel or from occurrence of dislodging a parietal thrombus/parietal atheroma free from the blood vessel wall.

[2] In the tubular medical treatment instrument indwelling device 1 recited in the above [1], said front tip 40 has a forward end side taper portion 52 that is arranged on the forward end side and has an outer diameter that increases from the forward end side to the base end side, a base end portion 56 arranged on the base end side, and a body portion 54 arranged between said forward end side taper portion 52 and said base end portion 56, and said engaging portion 42 is preferably formed in said body portion 54.

In the above constitution that is so provided, the sheath 10 covers the body portion 54 up to a predetermined position (position on the more forward end side than the position of the engaging portion), so that the engaging portion 42 can be hidden inside said sheath.

[3] In the tubular medical treatment instrument indwelling device 1 recited in the above [2], preferably, a groove portion 66 extending toward said forward end taper portion 52 from said base end portion 56 is formed in said body portion 54.

In the above constitution that is so provided, when a saline solution is filled in the sheath, air remaining in the sheath comes to be evacuated or discharged outside the sheath through the groove portion, so that the evacuation of air in the sheath (evacuation degree) can be improved.

[4] In the tubular medical treatment instrument indwelling device 1 recited in any one of the above [1] to [3], said engaging portion 42 is preferably in a form of a groove having a predetermined depth.

When the engagement portion provided in the tubular medical treatment instrument is a hook H, the thus-provided constitution enables the engaging portion 42 to get stuck with the hook H in a relatively simple constitution. Further, since the engaging portion 42 is in a form of a groove having a predetermined depth (groove for hook engagement or hook engagement groove), the outer diameter of the front tip is in no case increased as compared with an engaging portion in a form of a projection having a predetermined height.

[5] In the tubular medical treatment instrument indwelling device 1 recited in any one of the above [1] to [4], preferably, said base end portion 56 is formed in a tapered form in which the outer diameter thereof is decreased from the forward end side to the base end side.

In the above constitution that is so provided, the front tip 40 can be easily inserted when it is inserted into the sheath 10.

According to this invention, further, there is also provided a front tip for a tubular medical treatment instrument indwelling device.

[6] The front tip 40 for the tubular medical treatment instrument indwelling device, provided by this invention, which comprises a forward end side taper portion 52 that is arranged on the forward end side and has an outer diameter that is increased toward the base end side from the forward end side, a base end portion 56 arranged on the base end side, and a body portion 54 arranged between said forward end side taper portion and said base end portion, wherein there formed an engaging portion 42 in said body portion 54, engageable with an engagement portion H provided in the tubular medical treatment instrument SG.

According to the front tip 40 for the tubular medical treatment instrument indwelling device, provided by this invention, therefore, the engaging portion is formed in the body portion, so that there can be employed a constitution in which the front tip of this invention is attached to the tubular medical treatment instrument indwelling device and covered with a sheath up to a predetermined position (position on a more forward side than the position of the engaging position), whereby the engaging portion is hidden inside the sheath.

That is, when the front tip of this invention is used with the tubular medical treatment instrument indwelling device, the engaging portion is in no case exposed outside when it is moved inside a blood vessel, etc., so that the engaging portion can be constrained from inflicting a damage to a blood vessel, etc., by getting stuck on a blood vessel wall, or from dislodging a parietal thrombus/parietal atheroma free from the blood vessel wall.

[7] In the front tip 40 for the tubular medical treatment instrument indwelling device as recited in the above [6], preferably, said engaging portion 42 is in a form of a groove having a predetermined depth.

When the engagement portion provided in the tubular medical treatment instrument is a hook, the above constitution provided as described above enables the engaging portion to get stuck with the hook reliably in a relatively simple constitution. Further, since the engaging portion has a predetermined depth (groove for being engaged with the hook), the outer diameter of the front tip is in no case increased as compared with an engaging portion that is in a form of a projection having a predetermined height.

The feature of the tubular medical treatment instrument indwelling device recited in the above [5] can be also applied to the front tip for the tubular medical treatment instrument indwelling device, provided by this invention.

Reference numerals or parenthesized reference numerals added to members, etc., described in claims and this section (section of Means to Solve the Problems) are used for making it easy to understand the contents described in the claims and this section, and they shall not limit the technical contents described in the claims and this section.

EMBODIMENTS FOR CARRYING OUT THE INVENTION

The tubular medical treatment instrument indwelling device and the front tip for the tubular medical treatment instrument indwelling device (to be sometimes simply referred to as "front tip" hereinafter), provided by this invention, will be explained below with reference to embodiments shown in drawings.

[First Embodiment of the Invention]

The constitution of a tubular medical treatment instrument indwelling device 1 according to a first embodiment of this invention will be explained with reference to FIG. 1.

Figure 1A:
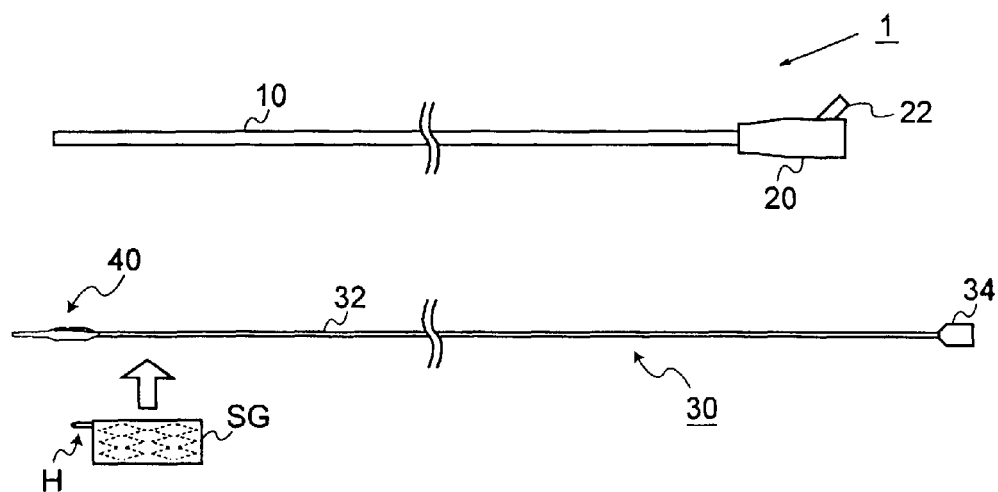
FIGS. 1a-c shows drawings for explaining the tubular medical treatment instrument indwelling device 1 according to a first embodiment of this invention.
Figure 1B:
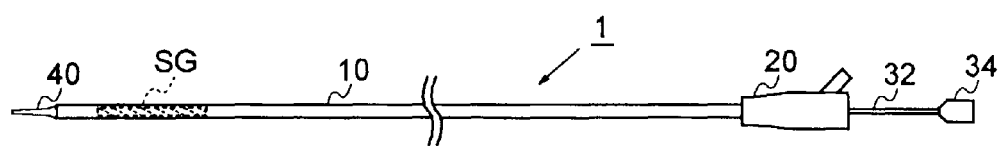
Figure 1C:
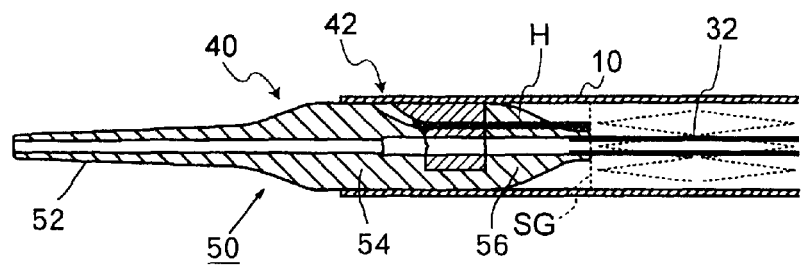
Figure 2A:
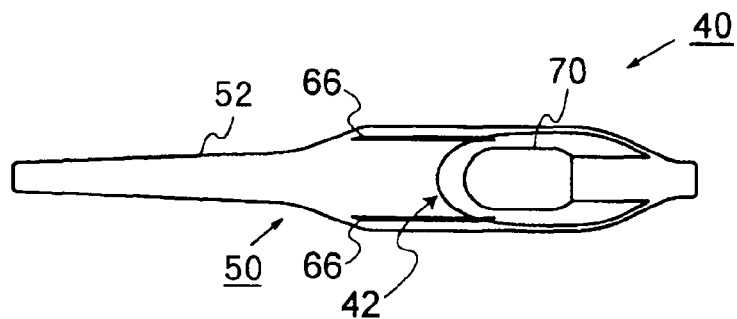
FIGS. 2a-e shows drawings for explaining the front tip 40.
Figure 2B:
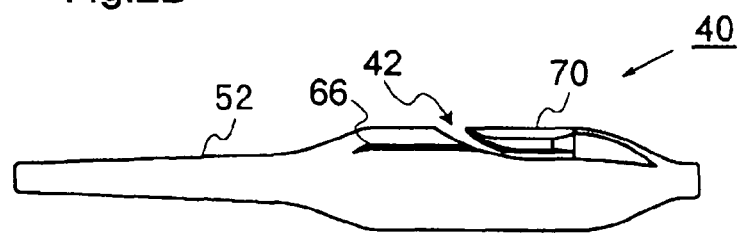
Figure 2C:
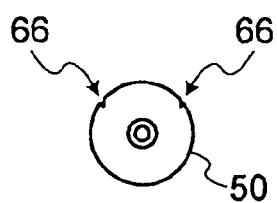
Figure 2D:
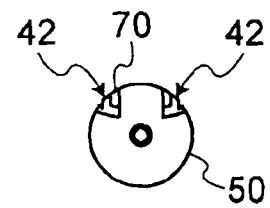
Figure 2E:
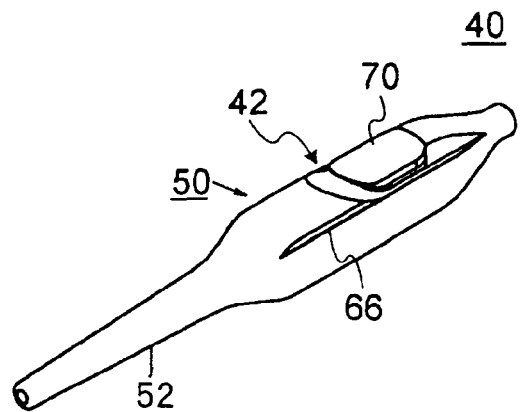

FIGS. 1A to 1C are drawings for explaining the tubular medical treatment instrument indwelling device 1 according to the first embodiment of this invention. In more detail, FIG. 1A shows drawings of members that constitute the tubular medical treatment instrument indwelling device 1 and a stent graft SG. FIG. 1B shows drawing of a state in which the members are assembled and the stent graft SG is arranged inside the tubular medical treatment instrument indwelling device 1. FIG. 1C shows an enlarged cross-sectional view of the forward end portion and its vicinity (portion of a front tip 40 and its vicinity) of the tubular medical treatment instrument indwelling device 1. FIG. 1 does not necessarily show exact sizes (lengths and dimensions of diameters, etc.), forms or dimensional ratios of the members that constitute the tubular medical treatment instrument indwelling device and the stent graft SG, but rather shows them schematically.

In the present specification, the "forward end side" refers to the distal side of the tubular medical treatment instrument indwelling device 1 when the device 1 is viewed from a user, and it indicates the front tip 40 side in FIG. 1B. Further, the "base end side" refers to the proximal side of the tubular medical treatment instrument indwelling device 1 when the device 1 is viewed from a user, and it indicates the side of a wire introduction inlet 34 such as a guide wire in FIG. 1B.

The tubular medical treatment instrument indwelling device 1 according to the first embodiment of this invention is a stent graft indwelling device for placing a radially expandable stent graft SG (tubular medical treatment instrument) at a diseased site. As shown in FIG. 1, it comprises a rod member 30 and a front tip 40, in which the rod member is constituted so as to be movable forward and backward inside the tubular sheath (in the lumen of the sheath 10) along the axial direction of the sheath 10 (in the longitudinal direction of the sheath 10), and the front tip 40 is arranged in the forward or front end portion of the rod member 30.

The stent graft SG as a tubular medical treatment instrument that is loaded into the tubular medical treatment instrument indwelling device 1, has, for example, (while parts of the explanation are made without referring to the drawings,) a self-expandable stent portion which is formed of a metal small-gage wire, folded up in a zigzag form, and shaped into a nearly cylindrical form, a graft portion which is sutured and fixed on the stent portion the way it covers the outer circumference of it, and a hook H which is provided on its forward end portion, as an engagement portion (for example, see FIG. 1A and FIG. 1C), while its showing by drawings is omitted.

While materials for constituting the stent portion of the stent graft SG may be a resin, the stent portion is preferably composed of a metal small-gage wire. The material for the metal small-gage wire constituting the stent portion is preferably selected, for example, from stainless steels such as SUS316L, etc., and known metals or metal alloys typified by Ni—Ti alloy, Cu—Zn alloy, Ni—Al alloy, and titanium alloy, etc.

The material for constituting the graft portion is preferably selected, for example, from fluorine resins such as PTFE (polytetrafluoroethylene), etc., and polyester resins such as polyethylene terephthalate, etc. The graft portion made from any one of these resin materials has relatively high biocompatibility and durability and also has good chemical stability.

The stent graft that can be used with the tubular medical treatment instrument indwelling device 1 according to the first embodiment (tubular medical treatment instrument indwelling device of this invention) is not limited to the stent graft that has the above constitution and that formed from the above material(s), and there may be used a known stent graft that is different in constitution and material.

The sheath 10 in this invention is a tubular elongated member formed from a flexible material, and it is a member in which a rod main body 32 and the stent graft SG can be held inside its tubular body. Examples of the above flexible material preferably include a synthetic resin (or elastomer thereof) that is selected from a fluorine resin, a polyamide resin, a polyethylene resin, and a polyvinyl chloride resin, etc., and that preferably has biocompatibility, resin compounds obtained by mixing these resins with other material(s), multi-layer tubular structures obtained, for example, by multi-layer-extrusion of these synthetic resins, and composite tubular materials formed from these synthetic resins and a metal wire.

The base end portion of the sheath 10 is provided with a sheath base portion 20 as shown in FIG. 1A. The sheath base portion 20 is provided with a liquid filling charging port 22 for charging or filling, for example, a saline solution into the sheath 10. There is preferably employed a constitution in which a cap with a valve, that is not shown here, is fitted on the base end side of the sheath base portion 20, to seal blood, etc., from leaking when the rod member 30 is inserted into the sheath 10.

While description referring to drawings is omitted, the sheath 10 is constituted such that its inner diameter is larger than the outer diameter of the rod main body 32 of the rod member 30 as will be described later. In this manner, the rod member 30 can be arranged and set inside the sheath 10.

Meanwhile, the stent graft SG is a device delivered to an indwelling site (diseased site) along through the inside of a blood vessel in a compressed state, with reduced diameter, and the rod member 30 is a member used to push and expose the stent graft SG in the above compressed state from the forward end of the sheath at the intended indwelling site. The rod member 30 has the rod main body 32 and a wire introduction inlet 34 arranged on the base end side of the rod main body 32. The rod member 30 has a constitution in which the stent graft SG in a compressed state is held in the vicinity of the forward end portion of the rod main body 32.

The materials for constituting the rod main body 32 are preferably selected, for example, from those materials having a proper hardness and flexibility which include resins such as a plastic or elastomer or metals.

Although a description in reference to drawings is omitted, the rod main body 32 preferably has, for example, a guide wire lumen for passing a guide wire through its interior and a trigger wire lumen for passing a trigger wire that is used to expand the compressed stent graft SG at a diseased state, the guide wire lumen and the trigger wire lumen being formed along the axial direction (in the longitudinal direction of the rod member 30) of the rod member 30.

(Front Tip)

The constitution of the front tip 40 will be explained below.

FIG. 2 shows drawings for generally explaining the overview of the front tip 40. FIG. 2A is a plan view of the front tip 40 viewed from above, FIG. 2B is a side view of the front tip 40 viewed from a lateral side, FIG. 2C is a view obtained by viewing the front tip 40 from the forward end side, FIG. 2D is a view obtained by viewing the front tip 40 from the base end side (sheath 10 side), and FIG. 2E is a perspective view of the front tip 40.

As shown in FIG. 2, the front tip 40 is composed of a first member 50 that determines the basic form of said front tip 40 and a second member 70. The second member 70 is fitted into a concave portion 64 formed in a body portion 54 (to be described later) in said first member 50, and thereby forming an engaging portion 42.

The constitution of the front tip 40 (first member 50 and second member 70) will be explained further in detail with reference to FIGS. 3 to 5.

FIG. 3 shows drawings for explaining the first member 50 of the front tip 40. FIG. 3A is a plan view of the first member 50 viewed from above, FIG. 3B is a side view of the first member 50 viewed from a lateral side, FIG. 3C is a cross-sectional view of the first member 50, FIG. 3D is a cross-sectional view taken along A-A line in FIG. 3B, FIG. 3E is an enlarged view of a portion indicated by a symbol P in FIG. 3D, and FIG. 3F is cross-sectional view taken along B-B line in FIG. 3B.

FIG. 4 shows drawings for explaining the second member 70 of the front tip 40. FIG. 4A is a plan view of the second member 70 viewed from above, FIG. 4B is a side view of the second member 70 viewed from a lateral side, FIG. 4C is a view obtained by viewing the second member 70 from the base end side (sheath 10 side), and FIG. 4D is a transverse cross-sectional view of the second member 70. In FIGS. 4A to 4C, the first member 50 is shown by broken lines, and the second member 70 is shown by solid lines, for providing a easy understanding of arrangement positions of the second member 70 to the first member 50.

Figure 5A:
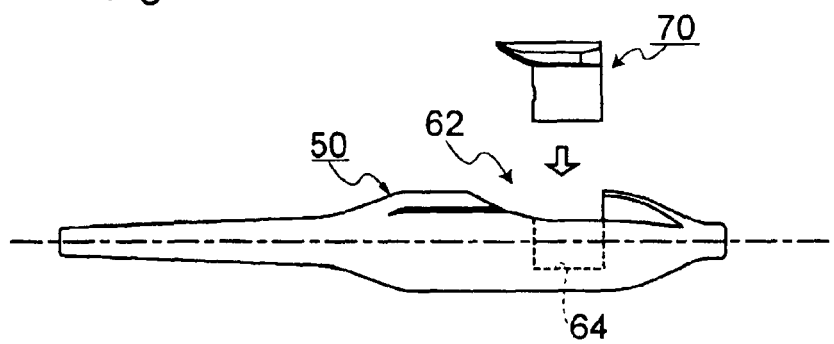
FIGS. 5a-b shows drawings for explaining the front tip 40.
Figure 5B:
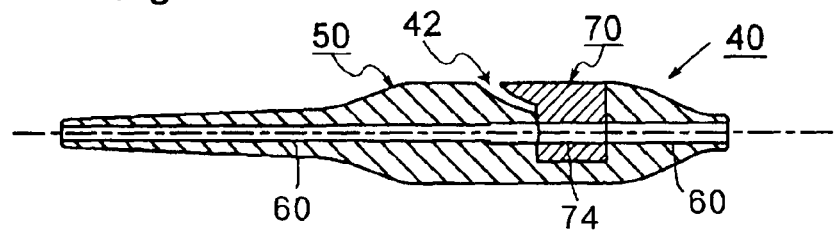

FIG. 5 shows drawings for explaining the front tip 40. FIG. 5A is a breakdown-view of the first member 50 and the second member 70, and FIG. 5B is a transverse cross-sectional view of the front tip 40 in which the second member 70 is fitted into the first member 50.

The front tip 40 in principle has the function to seal the forward end of the sheath 10 to prevent a body fluid such as a blood, etc., from entering the interiors of the sheath 10 and the stent graft SG.

As described above, the front tip 40 is basically constituted of the two members such as the first member 40 and the second member 70 adapted to be fitted into part of the first member 50 as shown in FIGS. 2 and 5. These first and second members 50 and 70 will be explained in detail later. There is employed a constitution in which the hook H of the stent graft SG (see FIG. 1A and FIG. 1C) can be engaged with the engaging portion 42 which is formed by the first member 50 and the second member 70.

(First Member)

As shown in FIG. 3, the first member 50 has a forward end side taper portion 52 that is arranged on the forward end side and is so formed as to have an outer diameter that is increased from the forward end side to the base end side, a base end portion 56 that is arranged on the base end side and is so formed in a tapered form as to have an outer diameter that is decreased from the forward end side to the base end side, a body portion 54 arranged between the forward end taper portion 52 and the base end portion 56, a forward end side notched portion 58, a base end side opening portion 59, a notched portion 62 formed on the upper portion of the first member 50, a concave portion 64 provided in the bottom of said notched portion 62, and two groove portions 66. Further, inside the first member 50 is formed a through hole 60 connecting the forward end side opening portion 58 and the base end side opening portion 59 (through hole making them communicated).

(Notched Portion)

The notched portion 62 will be specifically explained. The notched portion 62 is provided in a region ranging from the body portion 54 in the middle of the first member 50 to the base end portion 56. The body portion 54 has a region ranging from the forward end side to the base end side hollowed out until a predetermined depth is reached as shown in FIG. 3B. In the base end portion 56, two sides thereof are cut and removed nearly in the form of a V-letter with retaining a central portion C as shown in FIGS. 3A and 3F.

Figure 3A:
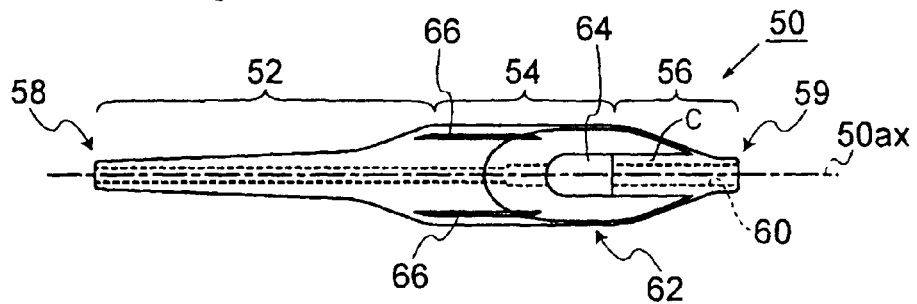
FIGS. 3a-f shows drawings for explaining the first member 50 of the front tip 40.
Figure 3B:
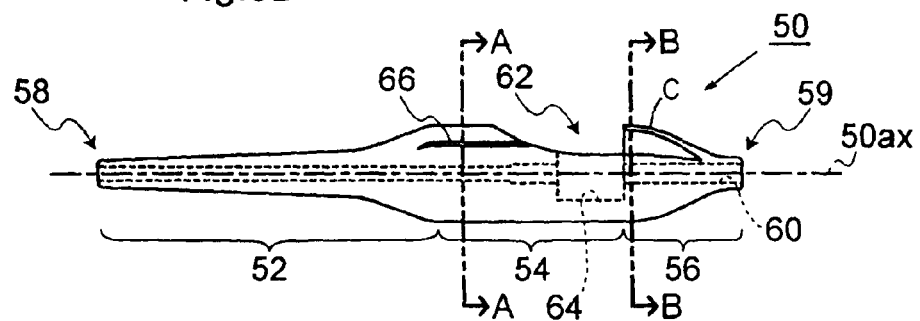
Figure 3C:
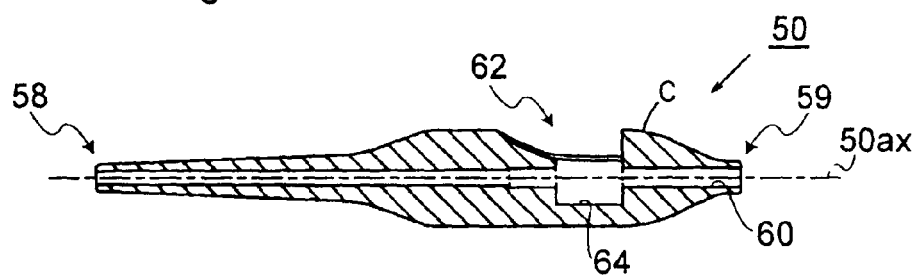
Figure 3D:
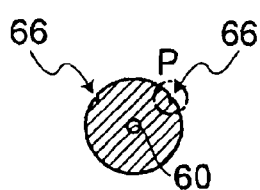
Figure 3E:
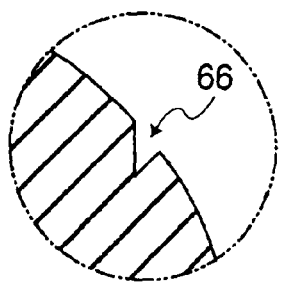
Figure 3F:
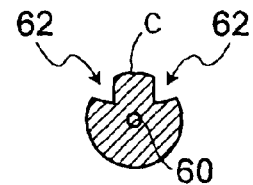

The groove portions 66 are formed in a region ranging from part of the notched portion 62 formed in the body portion 54 to part of the forward end side taper portion 52, as shown in FIGS. 3A and 3B. The groove portions 66 are grooves having a V-letter-shaped cross section each as shown in FIGS. 3D and 3E.

(Second Member)

Figure 4A:
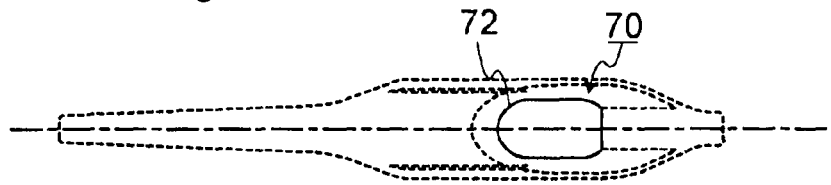
FIGS. 4a-d shows drawings for explaining the second member 70 of the front tip 40.
Figure 4B:
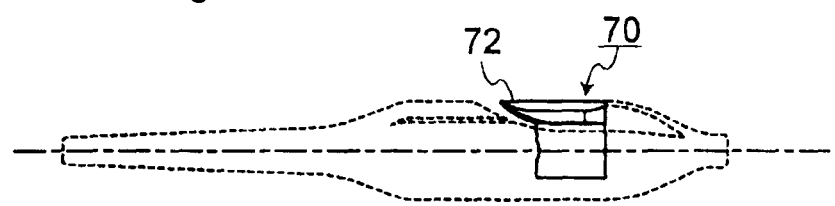
Figure 4C:
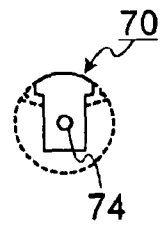
Figure 4D:
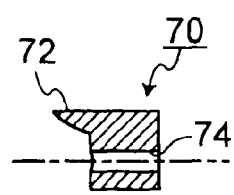

As shown in FIGS. 4B and 4D, the second member 70 has an eaves-shaped portion 72 having an upper portion of which the forward end side portion extends in the form of eaves, and has a constitution in which the lower portion of the eaves-shaped portion 72 extends downward to be engageable with, or fitted to, the concave portion 64 of the first member 50. Further, as shown in FIGS. 4C and 4D, a through hole 74 is formed in a predetermined position of the second member 70. This through hole 74 is so constituted as to communicate with the through hole 60 of the first member 50 when the second member 70 is fitted into the concave portion 64 of the first member 50 (see FIG. 5B).

These through holes 60 and 74 are used, for example, as guide wire lumens for passing a guide wire through them.

The materials for constituting the first and second members 50 and 70 can be preferably selected, for example, from various materials having proper hardness and flexibility such as synthetic resins (or their elastomers) composed of polyamide resins, polyurethane resins or polyvinyl chloride resins.

The first member 50 and the second member 70 may be constituted from the same material or may be constituted from different materials.

In the front tip 40 used in this invention, a contrast or imaging agent such as barium sulfate, etc., may be added, as an auxiliary material, to the first member 50 and the second member 70. In this case, there may be employed a constitution in which different concentrations of the contrast agent are added to the first member and the second member and, for example, the second member 70 is caused to have a lower concentration than the first member 50. However, they may be caused to have opposite concentrations profile. Barium sulfate, etc., are radiation-impermeable substances, so that the position, direction, etc., can be figured out by monitoring a difference in concentration during contrast-imaging procedure.

The front tip (the first member and second member) in this invention can be formed, for example, by melt injection-molding these materials.

As shown in FIG. 5, the second member 70 is fitted into the concave portion 64 of the first member 50, whereby a groove having a predetermined depth (groove for hook engagement) is formed between the first member 50 and the second member 70. This groove performs the function of the engaging portion 42 of the front tip 40. The engaging portion 42 is positioned in the body portion 54 of the first member 50 (and the base end portion 56) as shown in FIG. 3.

As shown in FIG. 1C, when the forward end portion of the sheath 10 is sealed with the front tip 40, the front tip 40 is covered with the sheath 10 up to the vicinity of boundary portion of the forward end side taper portion 52 and the body portion 54 of the first member 50. In this situation, since the engaging portion 42 is positioned in the body portion 54 of the first member 50, it is secured that the engaging portion 42 is covered with the sheath 10. In other words, it can be said that the engaging portion 42 is formed in a position to be hidden inside the sheath 10 when the forward end portion of the sheath 10 is sealed with the front tip 40.

(Advantageous Effects)

(1) According to the thus-constituted tubular medical treatment instrument indwelling device 1 according to the first embodiment, the engaging portion 42 of the front tip 40 is formed in a position to be hidden inside the sheath 10 when the forward end portion of the sheath 10 is sealed with the front tip 40, so that the engaging portion 42 is no longer exposed outside when the indwelling device is moved in a blood vessel, etc. As a result, the thus hidden engaging portion 42 can be constrained from inflicting a damage to a blood vessel, by getting stuck on a blood vessel wall etc., or thus constrained from dislodging a parietal thrombus/parietal atheroma free from the blood vessel wall.

Therefore, the tubular medical treatment instrument indwelling device 1 according to the first embodiment is a tubular medical treatment instrument indwelling device that does not inflict a damage to a blood vessel, etc., or constrains to dislodge parietal thrombus/parietal atheroma free from the blood vessel wall.

In the tubular medical treatment instrument indwelling device 1 according to the first embodiment, the engaging portion 42 is formed in the body portion 54, so that the engaging portion 42 can be hidden inside the sheath 10 by covering the body 54 up to a predetermined position (position on the forwarder end side than the engaging portion 42 position).

(2) In the tubular medical treatment instrument indwelling device 1 according to the first embodiment, the groove portions 66 are formed in the body portion 54 as shown in FIGS. 3A and 3B. As is already described, these groove portions 66 are formed in a region ranging from part of the notched portion 62 formed in the body portion 54 to part of the forward end side taper portion 52 (see FIGS. 3A and 3B), and the notched portion 62 is located in a portion that is nearer to the base end side than the groove portions 66, so that air remaining in the sheath is discharged or evacuated extracted outside the sheath 10 through the notched portion 62 and the groove portions 66 when saline solution is filled in the sheath 10. Thus constituted, the evacuation of air in the sheath 10 (degree of discharge) can be improved.

That is, when a saline solution is filled, these can function as conduits for purging air to be discharged (notched portion 62 for purging and groove portions 66 for purging).

(3) In the tubular medical treatment instrument indwelling device 1 according to the first embodiment, the engaging portion 42 of the front tip 40 is so constituted as a groove having a predetermined depth, that the engaging portion 42 having a relatively simple constitution can get stuck steadily with the hook H of the stent graft SG. Further, since the engaging portion 42 is constituted as a groove having a predetermined depth, the outer diameter of the front tip 40 is in no case more increased as compared with an engaging portion 42 when that is constituted as a projection having a predetermined height.

(4) In the tubular medical treatment instrument indwelling device 1 according to the first embodiment, the base end portion 56 of the front tip 40 is formed in a tapered form in which the outer diameter thereof is decreased from the forward end side to the base end side, so that the front tip 40 can be easily inserted when the front tip 40 is to be inserted into the sheath 10.

(5) According to the front tip 40 according to the first embodiment, the engaging portion 42 is formed in the body portion 54, so that there can be employed a constitution in which the engaging portion 42 is hidden inside the sheath by attaching the front tip 40 according to the first embodiment to the tubular medical treatment instrument indwelling device and covering it up to a predetermined position of the body portion (position on the more forwarded side than the position of the engaging portion 42). That is, when the front tip 40 according to the first embodiment is used in the tubular medical treatment instrument indwelling device, the engaging portion is no longer exposed outside when the indwelling device is moved in a blood vessel, etc., so that the engaging portion can be constrained from damaging a blood vessel, etc., by getting stuck on a blood vessel wall, or dislodging parietal thrombus/parietal atheroma free from the blood vessel wall.

[Second Embodiment of the Invention]

Another embodiment of this invention, i.e., an embodiment (second embodiment) in which the front tip in the tubular medical treatment instrument indwelling device differs from that in First Embodiment will be explained below.

Figure 6A:
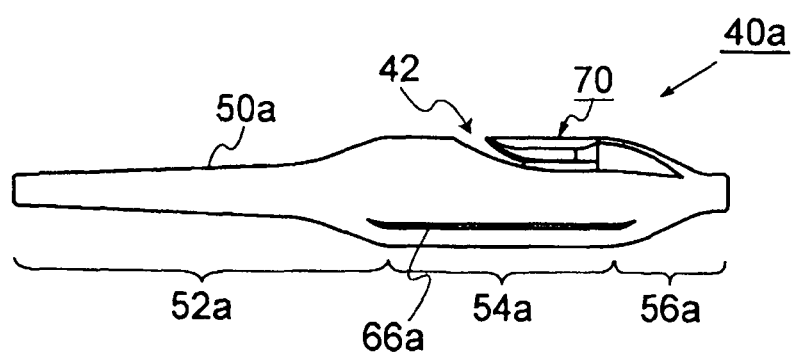
FIGS. 6a-b shows drawings for explaining the front tip 40a according to a second embodiment of this invention.
Figure 6B:
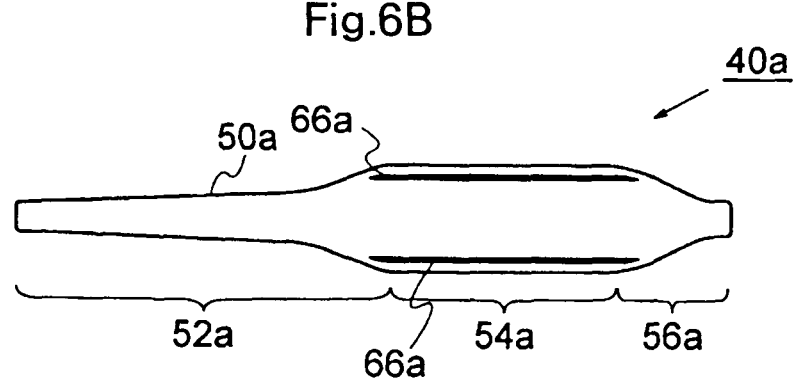

FIG. 6 shows drawings for explaining a front tip 40a according to the second embodiment of this invention. FIG. 6A is a side view of the front tip 40a viewed from a lateral side, and FIG. 6B is a bottom view of the front tip 40a viewed from below.

In FIG. 6, the same members as those in FIG. 3 are shown by the same reference numerals, and detailed explanations of them will be omitted.

The front tip 40a according to the second embodiment basically has a constitution similar to that of the front tip 40 according to the first embodiment, while it differs from the front tip 40 according to the first embodiment in position of groove portions 66a.

That is, in the front tip 40a according to the second embodiment, two groove portions 66a are formed in lower portions of the front tip 40a as shown in FIG. 6. The groove portions 66a are formed in a region ranging from a forward end side taper portion 52a to a base end portion 56a. The groove portions 66a are grooves each having the form of a V-letter in cross section although the showing thereof by drawings is omitted.

As described above, the front tip 40a according to the second embodiment differs from the front tip 40 according to the first embodiment in position of groove portions, while the engaging portion 42 of the front tip 40a is formed in a body portion 54a (in a position where it is hidden inside the sheath 10 when the forward end portion of the sheath 10 is sealed with the front tip 40a), so that the engaging portion 42 is in no case exposed outside when the indwelling device is moved inside a blood vessel, etc., like the case of the front tip 40 according to the first embodiment. As a result, the engaging portion can be kept from inflicting a damage to a blood vessel, etc., by getting stuck on a blood vessel wall, or from dislodging a parietal thrombus/parietal atheroma free from the blood vessel wall.

The front tip 40a according to the second embodiment has the same constitution as that of the front tip 40 according to the first embodiment except that the positions of the groove portions are different, so that the front tip 40a has relevant effects without any modification among those effects which the front tip 40 according to the first embodiment has. (In addition, the tubular medical treatment instrument indwelling device 1 having the front tip 40 may be depicted as 1, and the embodiment having the front tip 40a may be depicted as 1a.)

The tubular medical treatment instrument indwelling devices 1 and 1a and the front tips 40 and 40a for the tubular medical treatment instrument indwelling device have been explained hereinabove with reference to the first and second embodiments of this invention, while this invention shall not be limited to the above embodiments, and can be practiced in various embodiments so long as it does not extend beyond the gist thereof. For example, the following variants are possible.

(1) The above embodiments have been explained with reference to examples in which each of the front tips 40 and 40a is constituted from two members such as the first member and the second member, while this invention shall not be limited to these, and the first member and the second member may be a single member obtained by integrally forming the first and second members (a single member having a portion corresponding to the first member and a portion corresponding to the second member).

(2) The above embodiments have been explained with reference to a case where two groove portions 66 or 66a are formed in the front tip 40 or 40a, while this invention shall not be limited thereto, and there may be employed a case where one groove or three or more grooves are formed. Further, there may be employed a constitution in which the constitution of the second embodiment (grooves formed in the lower portion of the front tip and formed in a region ranging from the forward end taper portion to the base end portion) is added to the constitution of the first embodiment (two grooves extending in a region ranging from the notched portion to the forward end taper portion).

The above embodiments have been explained with reference to cases where the groove portions 66 or 66a are formed in the front tip 40 or 40a, while the above groove portions 66 or 66a are not necessarily required to be formed. In the front tip 40 or 40a having the above groove portions 66 or 66a formed thereon, that portion which comes in contact with a blood vessel has a relatively minor concavoconvex shape, and it can be hence said that the risk of, by the groove portions 66 or 66a, damaging a blood vessel, etc., or dislodging parietal thrombus/parietal atheroma free from the blood vessel wall is remarkably low. When the front tip has no groove portions 66 or 66a, a concavoconvex shape of that portion which comes in contact with a blood vessel can be removed, and hence the risk caused by such a concavoconvex shape can be brought close to zero without any limitation.

(3) The above embodiments have been explained with reference to examples in which the groove portions 66 or 66a each have the form of nearly a V-letter, while this invention shall not be limited thereto. The groove portions may have the form of nearly a U-letter or may have the form of nearly a semicircle.

(4) The above first embodiment has been explained with reference to the sheath base portion 20 provided with the liquid charging port 22, while this invention shall not be limited thereto. The sheath base portion may be provided with one or more ports different from the liquid charging port 22.

(5) The above first embodiment has been explained with reference to an example in which the engagement portion of the tubular medical treatment instrument is a hook, while this invention shall not be limited thereto. The engagement portion may be other engagement portion such as an engagement portion having a claw-shaped engagement means. Further, the engaging portion formed in the front tip shall not be limited to the above-described groove having a predetermined depth (groove for hook engagement), and it may be an engaging portion (e.g., a projection having a predetermined height) that is of a type and form matching up with the kind and form of the engagement portion.

(6) The above first embodiment shows an example of the stent graft SG having a hook H as a tubular medical treatment instrument, and explanation is given with a case where the tubular medical treatment instrument having such an engagement portion is placed for indwelling at a diseased site, while this invention shall not be limited thereto. Needless to say, the tubular medical treatment instrument indwelling device having the front tip for a tubular medical treatment instrument indwelling device, provided by this invention, may be applied when a tubular medical treatment instrument having no engagement portion is to be placed in a diseased site.

The above embodiments have been explained with reference to the stent graft indwelling device for placing the stent graft at a diseased site, while this invention shall not be limited thereto. This invention can be applied to a tubular medical treatment instrument indwelling device for placing a tubular medical treatment instrument other than the stent graft (e.g., a stent indwelling device for placing a stent in a diseased site).

INDUSTRIAL UTILITY

The tubular medical treatment instrument indwelling device and the front tip for the tubular medical treatment instrument indwelling device, provided by this invention, having a constitution in which the engaging portions is never exposed outside in a blood vessel, posses high industrial utility since they can effectively kept from inflicting a damage to a blood vessel, etc., or constrained form dislodging a parietal thrombus/parietal atheroma.

EXPLANATIONS OF REFERENCE NUMERALS OR SYMBOLS

1 Tubular medical treatment instrument indwelling device
10 Sheath
20 Sheath base portion
22 Liquid charging port
30 Rod member
32 Rod main body
34 Wire introduction inlet
40, 40a Front tip
42 Engaging portion
50, 50a First member
52, 52a Forward end side taper portion
54, 54a Body portion
56, 56a Base end portion
58 Forward end side opening portion
59 Base end side opening portion
60, 74 Through hole
62 Notched portion
64 Concave portion
66, 66a Groove portion
70 Second member
72 Eaves-shaped portion
H Hook
C Central portion of base end portion
SG Stent graft

The invention claimed is:

1. A tubular medical treatment instrument indwelling device for delivering a radially expandable tubular medical treatment instrument up to a diseased site and placing the same at the diseased site, comprising:
a tubular sheath having flexibility and being so constituted as to encase said tubular medical treatment instrument therein;
a rod member that is so constituted as to move forward and backward inside said sheath along an axial direction of said sheath; and
a front tip that is provided in a forward end portion of said rod member and includes, formed therein, a hook-shaped engaging portion being engageable with an engagement potation provided in said tubular medical treatment instrument;
said front tip being capable of sealing a forward end portion of said sheath in a state in which the front tip is engaged with said tubular medical treatment instrument, and
said hook-shaped engaging portion being formed in a position where the hook-shaped engaging portion is hidden inside said sheath when the forward end portion of said sheath is sealed with said front tip, wherein said front tip has a forward end side taper portion that is arranged on a forward end side of the front tip and has an outer diameter that increases from the forward end side to a base end side of the front tip, a base end portion arranged on the base end side, and a body portion arranged between said forward end side taper portion and said base end portion, and said hook-shaped engaging portion is formed in said body portion, wherein (a) said body portion has an untapered, elongated shape, an upper portion of said body portion being provided with a notched portion serving as the hook-shaped engaging portion, said upper portion of the body portion has a substantially hemisphere-surfaced shape, and said notched portion is formed at a middle portion of said hemisphere-surfaced upper portion of the body portion, in a shape of a V-shaped-cut extending obliquely into said body portion, and when the forward end portion of said sheath is sealed with said front tip, said V-shaped-cut notched portion is covered and hidden inside said sheath, and (b) a plurality of elongated air purging groove portions are provided in an outer surface of the body portion separate from said notched portion, starting at the notched portion, extending through the body portion and terminating at the forward end side taper portion, whereby said elongated groove portions are able to function as a conduit for purging air when the sheath is being filled with saline solution.

2. The tubular medical treatment instrument indwelling device as recited in claim 1, wherein said base end portion is formed in a tapered form in which an outer diameter thereof is decreased from the forward end side to the base end side.

3. A front tip for a tubular medical treatment instrument indwelling device for delivering a radially expandable tubular medical treatment instrument up to a diseased site and placing the same at the diseased site, said tubular medical treatment instrument being encased in a tubular sheath, said front tip comprising:

a forward end side taper portion that is arranged on a forward end side of the tip and has an outer diameter that is increased toward a base end side of the tip from the forward end side;

a base end portion arranged on the base end side;

a body portion arranged between said forward end side taper portion and said base end portion; and an engaging portion formed in said body portion and engageable with a hook-shaped engagement portion provided in a tubular medical treatment instrument, wherein (a) said body portion has an untapered, elongated shape, an upper portion of said body portion being provided with a notched portion serving as the engaging portion, said upper portion of the body portion has a substantially hemisphere-surfaced shape, and said notched portion is formed at a middle portion of said hemisphere-surfaced upper portion of the body portion, in a shape of a V-shaped-cut extending obliquely into said body portion, and when the forward end portion of said sheath is sealed with said front tip, said V-shaped-cut notched portion is covered and hidden inside said sheath, and (b) wherein an a plurality of elongated air-purging groove portions are provided in an outer surface of the body portion separate from said notched portion, starting at the notched portion, extending through the body portion and terminating at the forward end side taper portion, whereby said elongated groove portions are able to function as a conduit for purging air when the sheath is being filled with saline solution.

* * * * *